United States Patent
Wild et al.

(10) Patent No.: US 7,087,259 B2
(45) Date of Patent: Aug. 8, 2006

(54) CONCENTRATE COMPRISING GREEN TEA, GRAPE SKIN EXTRACT AND GRAPE EXTRACT, THE PRODUCTION THEREOF AND USE OF THE SAME

(75) Inventors: Hans-Peter Wild, Eppelheim (DE); Matthias Sass, Oftersheim (DE)

(73) Assignee: Capri Sun AG, Zug (CH)

( * ) Notice: Subject to any disclaimer, the term of this patent is extended or adjusted under 35 U.S.C. 154(b) by 0 days.

(21) Appl. No.: 10/491,229

(22) PCT Filed: Oct. 8, 2002

(86) PCT No.: PCT/EP02/11251

§ 371 (c)(1), (2), (4) Date: Aug. 10, 2004

(87) PCT Pub. No.: WO03/033005

PCT Pub. Date: Apr. 24, 2003

(65) Prior Publication Data
US 2005/0002961 A1    Jan. 6, 2005

(30) Foreign Application Priority Data
Oct. 15, 2001 (DE) ................................ 101 50 824

(51) Int. Cl.
*A23F 3/00* (2006.01)
(52) U.S. Cl. ........................ 426/597; 426/590; 426/599
(58) Field of Classification Search ................ 426/597, 426/590, 599
See application file for complete search history.

(56) References Cited

U.S. PATENT DOCUMENTS

| | | | |
|---|---|---|---|
| 5,484,594 A | | 1/1996 | Frangi et al. ............. 424/195.1 |
| 5,744,187 A | | 4/1998 | Gaynor |
| 5,780,086 A | * | 7/1998 | Kirksey et al. .......... 426/330.3 |
| 5,904,924 A | | 5/1999 | Gaynor |
| 6,036,991 A | * | 3/2000 | Humphrey et al. .......... 426/597 |
| 6,294,161 B1 | * | 9/2001 | Hiramoto et al. .......... 424/76.1 |
| 6,299,925 B1 | * | 10/2001 | Xiong et al. ................ 426/597 |
| 6,413,570 B1 | * | 7/2002 | Lehmberg et al. .......... 426/597 |
| 6,440,448 B1 | * | 8/2002 | Intelisano ................... 424/439 |
| 6,470,894 B1 | * | 10/2002 | Hersh et al. ................ 131/334 |

FOREIGN PATENT DOCUMENTS

| | | |
|---|---|---|
| DE | 200 17 291 U1 | 1/2001 |
| JP | 8-198770 * | 8/1996 |
| JP | 081-98770 | 8/1996 |
| WO | WO 01/10987 A1 | 2/2001 |

OTHER PUBLICATIONS

Derwent Abstract. Acc No. 2001-358164 for HU 9900693. Published Apr. 2001.*
Derwent Abstract. Acc No. 1993-376211 for SU 1775094. Published Nov. 1992.*
Derwent Abstract. Acc No. 1993-174356 for SU 1738216. Published Jun. 1992.*
Georg Thieme Verlag Stuttgart, Römpp Lexikon Chemie, 10th Edition, 1999, p. 3491 (see Attachment A for English translation of relevant portion of reference).
Georg Thieme Verlag Stuttgart, Römpp Lexikon Chemie, Naturstoffe, 1997, pp. 514-515 (see Attachment A for English translation of relevant portion of reference).
Watzl et al., Bioaktive Substanzen in Lebensmittein, 2nd Edition, 1999, pp. 4-7.
Springer-Verlag, Berlin, Heidelberg, Hagers-Handbuch der Pharmazeutischen Praxis, vol. 4, 5th Edition, 1992, pp. 628-638.
Internet: http://www.sysinet.com/re/product/ik__1/ix__1/pg__0/opt__/cid__329481/index.html.
Bodywise, 'Online,' XP02222675, http://www.bodywise.com/bwcatalog/PAS119E.asp, Nov. 27, 2002.
Dr. Myatt's, 'Online,' XP002222676, http://www.drmyattswellnessclub.com/myattswellnessclub9.html, Nov. 27, 2002.
International Search Report for PCT/EP02/11251.
Copy of Office Action for German Patent Application No. 101 50 824.7, dated Jun. 12, 2002.

* cited by examiner

*Primary Examiner*—Anthony Weier
(74) *Attorney, Agent, or Firm*—Kilyk & Bowersox, P.L.L.C.

(57) ABSTRACT

The present invention relates to a concentrate of vegetable extracts, has green-tea, grape-skin extract, and grape-seed extract. The concentrate of the invention can be used for the production of beverages having, despite a high polyphenol content, a low degree of bitterness acceptable to the consumer.

The present invention further relates to a process for the production of said concentrate.

20 Claims, No Drawings

CONCENTRATE COMPRISING GREEN TEA, GRAPE SKIN EXTRACT AND GRAPE EXTRACT, THE PRODUCTION THEREOF AND USE OF THE SAME

This application in a National Stage entry of International Application No. PCT/EP02/11251, filed Oct. 8, 2002, and claims the benefit of earlier filed German Patent Application No. 101 50 824.7 filed Oct. 15, 2001.

The present invention relates to a concentrate of vegetable extracts, to a process for the production thereof, and to the use thereof.

For many centuries health-relevant active substances have been included in human nourishment. Research in more recent years has indicated the preventive effects of secondary vegetable substances present in foodstuffs. A good overview of this subject is given in B. Watzl, C. Leitzmann, *Bioaktive Substanzen in Lebensmitteln*, 2nd Edition, 1999, Hippokrates Verlag, Stuttgart.

The largest group of these secondary vegetable substances comprises the polyphenols. The term "polyphenols" is a generic name for aromatic compounds containing at least two phenolic hydroxyl groups in the molecule (Römpp Lexikon Chemie, 10th Edition, 1999, Georg Thieme Verlag Stuttgart, pp 3491). Extracts of fruits, herbs, vegetables and other plants having a high content of phenolic components are of growing interest for the food industry since they are of an antioxidant nature and thus have a positive effect on health.

Green-tea or green-tea extracts exhibit a high content of polyphenols and are therefore preferably used for the production of beverages having a health potential.

Green-tea is almost inodorous and has an astringent and pleasantly bitter taste (cf Hagers Handbuch der Pharmazeutischen Praxis, Vol. 4, 5th Edition, 1992, Springer-Verlag, Berlin Heidelberg, pp 628 et seq). The bitter taste is caused by the polyphenols present in the tea. In green-tea there has mainly been found catechins, flavonol glycosides, bisflavonols and chlorogenic acid. The small-molecule components in these polyphenols, particularly the dimers, have capillary-sealing and anti-inflammatory effects.

In addition to its influence on health, green-tea is also esteemed as a mental stimulant; it increases concentration and promotes stamina.

Other substances having a high polyphenol content are extracts of grape skins and grape seeds. In this respect emphasis may be placed, in particular, on the content of oligomeric Procyanidins in extracts of grape seeds, a subgroup of the flavonoid polyphenols. Procyanidins are, by reason of their chemical structure, water-soluble and possess a low molecular weight (mol. wt. <7000), which makes them highly bioavailable. Physiologically, Procyanidins have hypotensive and antiarteriosclerotic properties, and they are regarded as being very efficient free-radical scavengers, which forms the basis of their antioxidant action (Römpp Lexikon Chemie, Naturstoffe, 1997, Georg Thieme Verlag, Stuttgart, p 514).

In the cell sap of numerous flowers and fruits there are present anthocyanidins having not only a coloring action but also an antioxidant potential. Anthocyanidins are derived from the anthocyanins, whose aglycons are representative thereof. The most important anthocyanidins include pelargonidin, cyanidin, delphinidin, paeonidin, petunidin, and malvidin. Malvidin-3-glucoside is present in, for example, bilberries or the skin of red grapes. Anthocyanidins are likewise regarded as belonging to the group of polyphenols.

Furthermore, the food-processing industry also makes use of extracts of fungi or fruits, which also have a positive influence on health. Thus, for example, extracts of the asiatic shiitake mushroom show immunostimulant actions. Fruit extracts of, for example, papaya or pineapple are rich in natural enzymes such as bromelain or papain, which are reported to have stimulating effect on the digestion.

However, it has been shown that with increasing antioxidant potential the degree of bitterness of the individual raw materials increases. This would be expected, since the antioxidant potential is mostly due to the phenolic ingredients in the starting materials and these phenolic components have a distinctly bitter taste. However, for product research departments in the food industry this means that the bitter taste becomes stronger with increasing health potential, and this has an undesirable influence on the consumer's acceptability of the product.

It is thus an object of the present invention to provide a concentrate exhibiting a high antioxidant potential combined with reduced bitterness, resulting in high sensory acceptability by the consumer.

This object is achieved according to the invention in a concentrate comprising green-tea, grape-skin extract, and grape-seed extract.

The present invention also relates to a process for the production of said concentrate and also to the use of the concentrate in food, particularly in a beverage.

Production of the extracts can be carried out by conventional methods. An alternative possibility is to use commercially available extracts.

The concentrate of the invention contains green-tea, in a preferred embodiment a green-tea extract. The tea extract is preferably obtained by aqueous extraction of the dried tea-leaves, this being carried out at an elevated temperature, preferably at a temperature of from 10° to 90° C. and more preferably a temperature of from 10° to 60° C.

The grape-skin extracts present in the concentrate of the invention are preferably obtained from the skins of red grapes. These extracts are obtained, for example, from the marc of the relevant grapes by aqueous extraction. Extracts are preferably added which contain malvidin-3-glycoside in a concentration of from 0.05 wt % to 10.0 wt %, preferably from 0.1 wt % to 4.0 wt %, and more preferably from 0.4 wt % to 1.0 wt %.

Furthermore, the concentrate of the invention contains extracts of grape seeds, preferably extracts containing oligomeric procyanidins in a concentration between 20 wt % and 95 wt % and preferably between 20 wt % and 60 wt %. In a preferred process for the production of the extracts, grape seeds are ground and the homogenizate extracted with water or water/ethanol mixtures.

The concentrate of the invention further contains extracts of edible fungi, such as shiitake (*Lentinus edodes*), maitake (*Grifola Frondosa*), or reishi (*Lucid Ganoderma*). Extraction of the fungi can be carried out as follows: fresh fungi are air-dried and then ground. Using water as solvent the fungal mash is extracted and the isolated extract then dried.

In a preferred embodiment, extracts of fruits can be added to the concentrate of the invention. Examples of suitable fruits are papaya, pineapple, apricot, mango, peach, and banana. Extracts of papaya and/or pineapple are preferably added. In a preferred process for the production of a fruit extract, the fruits are mechanically comminuted until they exhibit a pasty consistency. This mixture is squeezed by means of a squeezer and then filtered. The resulting fruit juice can, if required, be inspissated to a desired concentration by conventional methods.

Furthermore, vitamins can be added to the concentrate of the invention. Examples comprise water-soluble vitamins, such as vitamin $B_1$, vitamin $B_2$, vitamin $B_6$, vitamin $B_{12}$, vitamin C, and vitamin H (biotin), nicain, pantothenic acid or folic acid and lipovitamins, such as, provitamin A (beta-carotene), vitamin E, vitamin K, vitamin D. Particular preference is given to vitamin C.

The vitamins are added to the concentrate of the invention preferably in powder form or, in the case of lipovitamins, in a water-dispersible form. Usual amounts are between 0.1 wt % and 10.0 wt % and preferably between 0.5 wt % and 3.5 wt %.

In addition, mineral matter and/or nutritional trace elements, such as calcium, magnesium, zinc, selenium, iron, and chromium, can be added to the concentrate of the invention. Of these, selenium is preferred. The amount of mineral matter present in the concentrate of the invention depends on the nature of the mineral matter and the specific requirements. It is generally in the range of from 0.1 to 10 wt % and preferably in the range of from 0.2 to 8 wt %.

Moreover, the concentrate of the invention may contain at least one flavoring agent but preferably a combination of flavoring agents. The flavoring ingredients used can be natural, nature-identical and/or non-natural flavoring ingredients. Preferably natural flavors are used. The flavoring agent or the combination of flavoring agents is preferably one which imparts a fruity, fresh, or exotic taste to the beverage or other food obtained using the concentrate of the invention. The concentration of flavoring agent or combination of flavoring agents is usually from 0.1 to 5 wt % and preferably from 0.5 to 3.5 wt %.

Other additives that are commonly used in foodstuffs can be added to the concentrate of the invention. These additives may be, for example, acidifiers, such as citric acid, lactic acid, malic acid, and phosphoric acid; stabilizing agents, such as carob bean flour, pectin, and guar kernel flour; thickeners, such as xanthan gum, gellan, alginates, and gum arabic; sweetening agents, such as fructose, sucrose, invert sugar, and honey; or non-caloric sweeteners, such as aspartam, acesulfam K, saccharin, cyclamate, neohesperidin, thaumatin, and sucralose.

The concentration of the ingredients in the concentrate of the invention is preferably in the range of from 5.0 wt % to 20.0 wt % for the green-tea extract, from 10.0 wt % to 60.0 wt % for the grape-skin extract, from 0.5 wt % to 5.0 wt % for the grape-seed extract, and from 0.1 wt % to 5.0 wt % for the fungus extract (based on the total weight of the concentrate).

Special preference is given to concentrations of from 10.0 wt % to 15.0 wt % for green-tea, from 40.0 wt % to 50.0 wt % for the grape-skin extract, from 1.0 wt % to 3.0 wt % for the grape-seed extract, and from 0.1 wt % to 1.0 wt % for the fungus extract.

In order to produce the concentrate of the invention, the individual ingredients are intermixed. Powdered raw materials are completely dissolved in water prior to addition. During the preparation of the mixture, it is continuously stirred in order to obtain a homogeneous mixture. For preservation purposes the concentrate can be pasteurized.

The concentrate of the invention can be in the form of a liquid or a dried solid.

In order to obtain the concentrate in dry form, water is extracted from the mixed extracts in known manner, preferably by spray drying. Spray drying is an efficient method of transforming liquids to powder. Thus it is possible to obtain a powder having specific physical properties, such as flowability, residual water content, or density. At the same time the properties of the flavoring ingredients present therein can be controlled with reference to quality or release characteristics (A. Nilesen, J. Getler in Flavourings, Wiley-VCH Verlag GmbH Weinheim, 1998, pp 88 et seq).

The concentrate of the invention can be processed in conventional manner to tablets, granules, or powders. Examples of tablets of the invention include non-coated tablets in the form of compacts, including effervescent tablets, film tablets, and dragees.

The concentrate of the invention can be used for the production of beverages, for example, by dilution of a liquid concentrate or by dissolution of a powder, tablet, or granules in water or in cold or hot beverages, such as fruit juices or tea.

Furthermore, the concentrate of the invention can be added as supplementary food to other foodstuffs, such as mueslis, dairy products, eg, yoghurt, curd products, and permanent bakery goods.

The invention is explained in greater detail with reference to the following examples.

EXAMPLE 1

Various concentrates were prepared in the proportions given in Table 1. The extracts used in the concentrate were produced in the following manner:

Green-tea Extract coarsely ground green-tea-leaves are mixed with 3 times their weight of water having a temperature of 60° C. and, following a contact time of 30 minutes, the leaf residues are separated by centrifugation. The resulting extract is concentrated by film evaporation down to a dry mass of 60% mas.

Grape-skin Extract grape marc is placed in an extraction tank in which the solvent (water having a temperature of 40° C.) is pumped countercurrently through the marc. The isolated crude extract is filtered and then concentrated to a dry mass of 30% mas.

Grape-seed Extract grape seeds are ground and extracted in an extraction tank countercurrently to a water/ethanol mixture at 40° C. The alcohol is removed from the isolated extract by distillation and the residue is dried.

Fungus Extract dried fungi are ground and countercurrently extracted with water. The insoluble components are separated by centrifugation and the isolated extract is dried to a powder.

The total phenolic content and the antioxidant potential of the concentrates were determined. The phenolic content was determined photometrically as specified in the following paper:

V-L. Singelton; J. A. Rossi Colorimetry of Total Phenolics with Phosphomolybdic-phosphotungstic Acid Reagents. Am. J. Enol. Vitic. 1965, 16, 144.

The total phenolic content is "calculated as gallic acid" and stated in mg/L.

For sampling preparation the samples are diluted to a total phenolic content (calculated as gallic acid) of 50–500 mg/L.

The antioxidant potential was determined by the TEAC method. TEAC is an abbreviation for Trolox Equivalent Antioxidant Capacity and describes a method of determining the antioxidant capacity of a substance in vitro compared with a water-soluble vitamin E equivalent ("trolox"). The process is described, for example, in the following paper:

Re, R.; Pellegrini, N.; Proteggente, A.; Yang, M.; Rice-Evans, C. Antioxidant Activity Applying an Improved Abts Radical Cation Decoloratization Assay. Free Radical Biology & Medicine 1999, 26, 1231.

The results are listed in Table 1.

TABLE 1

|   | Green-tea extract | Grape-skin extract | Grape-seed extract | Fungus extract | Vitamin C | Total phenolics [mg/L] | TEAC antioxidant findings |
|---|---|---|---|---|---|---|---|
| 1 | 3.0 g/L | 0 | 0 | 0 | 0 | 540 | 9.15 |
| 2 | 0 | 12.0 g/L | 0 | 0 | 0 | 300 | 4.44 |
| 3 | 0 | 0 | 0.5 g/L | 0 | 0 | 315 | 3.34 |
| 4 | 0 | 0 | 0 | 0.1 g/L | 0 | 0 | 0 |
| 5 | 0 | 0 | 0 | 0 | 0.3 g/L | 0 | 1.47 |
| 6 | 3.0 g/L | 12.0 g/L | 0 | 0 | 0 | 840 | 13.6 |
| 7 | 3.0 g/L | 0 | 0.5 g/L | 0 | 0 | 855 | 12.5 |
| 8 | 0 | 12.0 g/L | 0.5 g/L | 0 | 0 | 615 | 7.8 |
| 9 | 0 | 12.0 g/L | 0.5 g/L | 0.1 g/L | 0.3 g/L | 615 | 9.3 |
| 10 | 3.0 g/L | 12.0 g/L | 0.5 g/L | 0.1 g/L | 0.3 g/L | 1155 | Theory 18.4 Found: 18.0 |

EXAMPLE 2

The bitterness of various extract combinations was determined by sensory tests. Production of the extracts used was carried out as described in Example 1. The extracts were intermixed and thoroughly mixed with a standardized mixture of invert syrup and citric acid to form a beverage. Prior to sensory comparison all of the beverages were set to the same ratio of sweet to sour so that bitterness alone was the evaluating criterion for the taster.

The assessments of trained tasters made it possible to place the degree of bitterness of the individual extracts in a continuous scale. The data obtained are recorded in a computer and checked for significant differences by statistical methods.

Table 2 lists the total phenolic content and the sensory results obtained on mixtures of different compositions based on a sugar/acid mixture not including carbonic acid.

TABLE 2

|   | Grape-skin extract | Green-tea extract | Grape-seed extract | Total phenolics [mg/L] | Bitterness |
|---|---|---|---|---|---|
| A | 12.0 g/l | 3.0 g/l | 0.5 g/L | 1120 | ○ |
| B | 12.0 g/l | 4.8 g/l | 0.0 g/L | 1120 | ++ |
| C | 12.0 g/l | 0.0 g/l | 1.37 g/L | 1120 | ++ |
| D | 44.8 g/l | 0.0 g/l | 0.0 g/L | 1120 | − |

Legend
○ = evaluation of blind sample: reference value
++ = significanty more bitter
+ = more bitter, but not significantly so
− = less bitter, but not significantly so
−− = significantly less bitter Compositions contain all three extracts (mixture A) showed only a slight degree of bitterness in a taste test. A diluted beverage containing only grape-skin extract was described as being slightly less bitter, but the TEAC value of this ingredient is lower than that of the other raw materials so that no highly antioxidant beverage can be obtained therewith. No significant difference could be determined by sensory testing, for which reason it must be certified as having the same degree of bitterness. Consequently, only the total mixture of all extracts shows a low degree of bitterness whilst having a high antioxidant potential.

The sensory tests show that a highly antioxidant concentrate can be provided by mixing the aforementioned raw materials or extracts and that the resulting concentrate exhibits, despite a high total phenolic content, a low degree of bitterness acceptable to the consumer. Apparently and—for the person skilled in the art—surprisingly, the bitter effects of the individual components cancel each other out.

The invention claimed is:

1. A concentrate, comprising
   5.0 wt % to 20.0 wt % of green-tea,
   10.0 wt % to 60.0 wt % of grape-skin extract, and
   0.5 wt % to 5.0 wt % of grape-seed extract based on the total weight of the concentrate.

2. The concentrate as defined in claim 1, further comprising a fungus extract.

3. The concentrate as defined in claim 2, wherein the fungus extract is an extract of shiitake mushrooms.

4. The concentrate as defined in claim 1, further comprising an extract of papaya and/or pineapple.

5. The concentrate as defined in claim 1, further comprising vitamin C.

6. The concentrate as defined in claim 1, wherein the grape-skin extract has a content of malvidin-3-glycoside of from 0.1 wt % to 1.0 wt %.

7. The concentrate as defined in claim 1, wherein the grape-seed extract has a content of oligomeric procyanidins of from 20 wt % to 95 wt %.

8. A process for the production of a concentrate as defined in claim 1, comprising the steps of mixing the raw materials and preserving the mixture by pasteurization.

9. A beverage comprising the concentrate of claim 1.

10. A foodstuff comprising the concentrate as defined in claim 1.

11. The concentrate as defined in claim 2, further comprising an extract of papaya and/or pineapple.

12. The concentrate as defined in claim 3, further comprising an extract of papaya and/or pineapple.

13. The concentrate as defined in claim 2, further comprising vitamin C.

14. The concentrate as defined in claim 3, further comprising vitamin C.

15. The concentrate as defined in claim 2, wherein the grape-skin extract has a content of malvidin-3-glycoside of from 0.1 wt % to 1.0 wt %.

16. The concentrate as defined in claim 3, wherein the grape-skin extract has a content of malvidin-3-glycoside of from 0.1 wt % to 1.0 wt %.

17. The concentrate as defined in claim 2, wherein the grape-seed extract has a content of oligomeric procyanidins of from 20 wt % to 95 wt %.

18. The concentrate as defined in claim 3, wherein the grape-seed extract has a content of oligomeric procyanidins of from 20 wt % to 95 wt %.

19. The concentrate as defined in claim 4, further comprising vitamin C.

20. The concentrate as defined in claim 4, wherein the grape-skin extract has a content of malvidin-3-glycoside of from 0.1 wt % to 1.0 wt %.

* * * * *

UNITED STATES PATENT AND TRADEMARK OFFICE
CERTIFICATE OF CORRECTION

PATENT NO. : 7,087,259 B2  Page 1 of 1
APPLICATION NO. : 10/491229
DATED : August 8, 2006
INVENTOR(S) : Wild et al.

It is certified that error appears in the above-identified patent and that said Letters Patent is hereby corrected as shown below:

On the title page item (54), and Col. 1, line 1,

"CONCENTRATE COMPRISING GREEN TEA, GRAPE SKIN EXTRACT AND GRAPE EXTRACT, THE PRODUCTION THEREOF AND USE OF THE SAME" should read --CONCENTRATE COMPRISING GREEN TEA, GRAPE SKIN EXTRACT AND GRAPE SEED EXTRACT, THE PRODUCTION THEREOF AND USE OF THE SAME--.

Signed and Sealed this

Twenty-first Day of November, 2006

JON W. DUDAS
*Director of the United States Patent and Trademark Office*